United States Patent [19]
Jackson et al.

[11] Patent Number: 5,652,658
[45] Date of Patent: Jul. 29, 1997

[54] GRID ARRAY INSPECTION SYSTEM AND METHOD

[75] Inventors: Robert Lea Jackson, Moorpark; Robert Cottle Boman, Simi Valley, both of Calif.

[73] Assignee: View Engineering, Inc., Simi Valley, Calif.

[21] Appl. No.: 138,776

[22] Filed: Oct. 19, 1993

[51] Int. Cl.$^6$ .................................. G01B 11/00
[52] U.S. Cl. .................. 356/398; 356/237; 356/376; 348/126
[58] Field of Search ................... 356/394, 398, 356/375, 376, 237; 348/87, 92, 125, 126; 382/145–150

[56] References Cited

U.S. PATENT DOCUMENTS

| | | | |
|---|---|---|---|
| 4,240,750 | 12/1980 | Kurtz et al. | 356/394 |
| 4,706,168 | 11/1987 | Weisner . | |
| 4,743,771 | 5/1988 | Sacks et al. . | |
| 4,872,052 | 10/1989 | Liudzius et al. . | |
| 4,891,529 | 1/1990 | Braun et al. . | |
| 5,024,529 | 6/1991 | Svetkoff et al. . | |
| 5,028,799 | 7/1991 | Chen et al. | 356/376 |
| 5,058,178 | 10/1991 | Ray . | |
| 5,162,866 | 11/1992 | Tomiya et al. | 356/398 |
| 5,192,983 | 3/1993 | Tokura . | |
| 5,206,705 | 4/1993 | Tokura | 356/376 |

OTHER PUBLICATIONS

Computer Design, vol. 25, No. 6, Mar. 1986, Littleton, Massachusetts, U.S., "Machine Vision Finds a Niche in Automated Inspection", pp. 46–50.

*Primary Examiner*—Hoa Q. Pham
*Attorney, Agent, or Firm*—Merchant, Gould, Smith, Edell, Welter & Schmidt, P.A.

[57] ABSTRACT

A high speed, high accuracy, three-dimensional inspection system for ball and pin grid assemblies. The system uses a three-dimensional scanner to gather data which is analyzed to yield height position measurements along with overall packaged dimensions. The grid array to be scanned is placed upon a fixture above a motion control table. The motion control system is controlled by a personal computer and has a high resolution. The parts can be presented in single trays, tray stackers, tubes or other carriers. Array packages are handled either manually or automatically. In the manual mode, arrays are loaded onto the fixture by hand before activated the image processing hardware. Alternatively, an automatic pick and place module may be used to load the grid array packages on the fixture. The fixture consists of a plate with a cavity the size of the grid array package being inspected. The size of the cavity can be adjusted to fit different size parts. In addition to the height and position measurements, measurements of spacing, coplanarity, standoff, grid pitch, ball diameter, ball position, and package warp can be performed. With regard to pin grid arrays, bent or missing pins can be detected with the system. With regard to ball grid arrays, missing balls can be detected.

12 Claims, 10 Drawing Sheets

GRID ARRAY INSPECTION SYSTEM AND METHOD

BACKGROUND OF THE INVENTION

1. Field of the Invention

This invention relates to an automatic grid array inspection system, and more particularly, to a automatic, non-contact inspection system for measuring the dimensional and geometric characteristics of semiconductor device packages.

2. Description of Related Art

The requirement for semiconductors to perform more functions at higher speeds while occupying less space on a printed circuit board has lead to the development and deployment of semiconductor packages that mount directly to the surface of the printed circuit board. Because these devices provide a high degree of functionality, they must provide for a large number of connections to provide input, output, power and ground. Grid array packages became necessary as the number of input/output connections for complex semiconductors became greater than could be accommodated in the limited area provided by only the sides of the semiconductor for interconnection, even in the finest pitch configurations. In addition, as complex semiconductors, such as processor chip packages, became physically larger, the length of the conductor path from the chip to the pad had to be minimized to provide high speed.

In order to reduce size and increase operating speed of the semiconductor those connections that contact the surface of the board must be very close to each other (fine pitch) and very close to the board thereby requiring very narrow and mechanically fragile leads. The length and geometry of the lead is critical as all connections must make contact with the wiring board pads without damage to the semiconductor, shorting or other connection defects. If one or more leads are too long then one or more other leads may not be able to provide a reliable contact to the board pad. If one or more leads are displaced or bent they may miss the pad or short circuit to an adjacent pad. It is critical therefore that the X and Y positions as well as the height and geometry of each connection is within the manufacturing tolerance of the semiconductor package design. Thus, rigorous manufacturing tolerances are required for the allowable X and Y position of an interconnect pin or ball as well as the heights of the pins or balls relative to the package body (coplanarity). In addition, pin grid arrays may exhibit defects not previously encountered in other package types (such as the compound bend of a pin).

Furthermore, the inspection method must be high speed in order to keep the cost of inspection to a minimum. Since the semiconductors have many interconnects (often above 200 and up to 400) and are physically large in area (up to 3.0 inches per side) the sensors, architecture and algorithms must support this requirement.

Previous systems provided measurement equipment for determining the dimensional lead integrity for semiconductor packages whose leads were on the outer periphery of the package, such as quad flat packs (QFP's) and single outline integrated circuit's. Visual imaging provided data used to identify broken leads, lack of leads, bent leads, and the angle of leads.

The methods and algorithms required for these measurements are well known but are not suitable to the construction and requirements of the pin and bump grid arrays whose interconnects are placed in multiple positions throughout the bottom area of the package.

Thus, the previous camera-based systems and techniques do not provide the three-dimensional data required for simultaneous position and height measurements. Side view images do not provide the mechanisms for inner lead measurements, bottom views do not provide height information.

Point laser triangulation systems provide adequate height information however, because of their limited measurement area and rates are much too slow for production volume testing.

Other techniques, such as structured light triangulation, typically does not provide the accuracy and flexibility required for the wide range of products that must be inspected.

The identification of compound bends in pin grid arrays by previous methods have proven unreliable and ineffective. A compound bend occurs when the intermediate portion of the pin is bent but the tip of the pin remains very close to the axis of projection from the device itself. This results in the tip of the pin being lower than if the pin was not bent, but the difference in height of the tip of the bent pin is not so great as to be greater than the overall deviation in all pin heights. Therefore, compound bends in pins can not be detected by height measurements at the pin tip alone.

In addition, previous art inspection systems are much larger in size. This increases the footprint of the system and makes utilization in the in-line manufacture and test of components difficult.

Finally, due to the physical characteristics of ball grids, accurate position data has been difficult to calculate. The surface of the solder balls is shiny and smooth, and gradually slopes to the surface of the package making ball position and height measurements difficult.

There is a need, therefore, for an automatic grid array inspection system for improving quality control of manufacturing of grid arrays. The system must be cost effective in determining the two-dimensional positioning of the balls and pins on the grid, in determining the height of each, in detecting bent pins, and in measuring coplanarity at rates for 100% inspection. Further, the system must perform the inspection with high speed and high accuracy.

SUMMARY OF THE INVENTION

To overcome the limitations of prior art described above, and to overcome other limitations that will become apparent upon reading and understanding the present specification, the present invention discloses a high speed, high accuracy, three-dimensional inspection system for ball and pin grid assemblies. A high speed, high resolution, three-dimensional scanner and imaging system is used to gather height information.

The collected data is then analyzed to yield height and position measurements along with overall packaged dimensions. The three-dimensional scanner only scans in one dimension and therefore must be continually repositioned (scanned) to provide full coverage of the grid arrays. A metrology-grade stage unit is provided to position the laser. A motion control system directs the movement of the metrology stage in response to commands received from a computer. Thus, the field of view of the laser scanner system may be matched to the dimensions of the package being inspected to provide inspection capabilities for the entire package.

The array to be scanned may be placed upon an inspection platform either manually or automatically. In the manual mode, arrays are loaded onto a fixture by hand and the image processing hardware is activated. The fixture consists of a plate with a cavity the size of the grid array package being inspected. The size of the cavity can be adjusted to fit different size grid arrays.

An automatic pick and place system may be used instead to load grid array packages on the fixture above the stage. The parts can be presented in single trays, tray stackers, tubes or other carriers. The automatic system has the capability of repackaging the parts as well. Thus, after inspection, parts can be placed back in the tray tubes and can be sorted according to pass or fail. In a third configuration, the inspection module was designed small so as to allow it to be incorporated in the in-line manufacture and test of the components.

In addition to the height and position measurements, the grid array inspection system can also measure element spacing, lead height, coplanarity, standoff, grid pitch, ball diameter, ball position, and package warp. The invention also includes a high speed algorithm means for determining, with a high degree of confidence, the presence of compound bends, a defect prevalent and unique to the pin grid array package.

These and various other advantages and features of novelty which characterize the invention or point out with particularity in the claims annexed hereto and form a part hereof. However, for a better understanding of the invention, its advantages, and the objects obtained by its use, reference should be made to the drawings which form a further part hereof, and to accompanying descriptive matter, in which there is illustrated and described specific examples of an apparatus in accordance with the invention.

BRIEF DESCRIPTION OF THE DRAWINGS

Referring now to the drawings in which like reference numbers represent corresponding parts throughout.

DETAILED DESCRIPTION OF THE INVENTION

In the following description of the preferred embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

The present invention provides a grid array inspection system. Inspection system identifies height and position data pertaining to both ball grid arrays and pin grid arrays.

Figure 1:
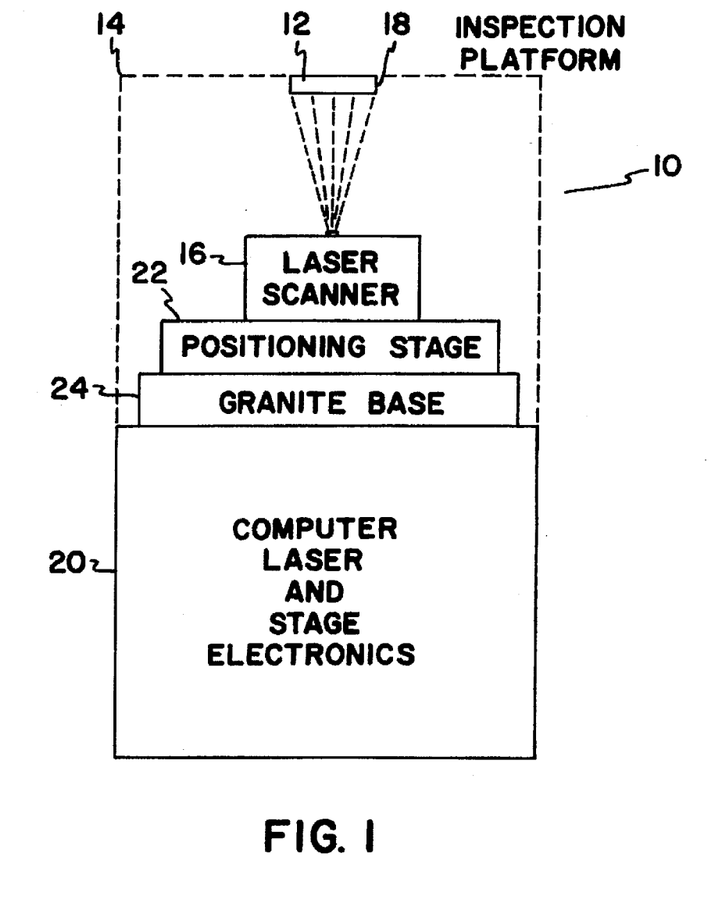
FIG. 1 is a system diagram of the grid array inspection system.

FIG. 1 illustrates an exemplary system 10 according to the present invention. The grid array 12 to be inspected is placed on a inspection platform 14 which is positioned over a scanning laser 16. Handling of the grid arrays 12 can be performed manually or automatically. The manual method involves merely placing the grid array 12 by hand in to a holding fixture 18. The fixture 18 consists of a plate with a cavity the size of the grid array package 12 being inspected. The size of the cavity can be adjusted to fit different size grid arrays 12.

An automatic system (not shown) uses a pick and place module to load the grid array packages 12 on the inspection platform 14. The grid array packages 12 can be presented in single trays, tray stackers or other carriers. The automatic system has the capability of repackaging the grid array packages 12 as well. Thus, after inspection, grid array packages 12 can be placed back in the output carriers and can be sorted according to pass or fail.

Preferably, the grid array inspection system 10 may comprise a three-dimensional scanner 16 for illuminating the grid arrays, such as the one described in U.S. Pat. No. 5,024,529 issued Jun. 18, 1991 to Donald J. Svetkoff et al., assigned to Synthetic Vision Systems, Inc., a wholly owned subsidiary of the assignee of the present invention, and incorporated by reference herein.

The three-dimensional scanner system provides an acousto-optic deflector together with associated lens element for scanning a beam of modulated laser light across the object to produce a telecentric, flat field scan. The system then delivers light reflected from the object to a small area position detector having a position-sensing direction. The light scattered from the object is first collected by a telecentric receiver lens. A spatial and polarization filtering plane is provided to control the polarization and acceptance angle of the collected light. The reduction or focusing lens is positioned immediately behind the filtering plane is utilized as a telescope objective. The lens system includes a negative cylinder lens having a relatively large focal length and a field lens having a relatively small focal length. The cylinder lens and the reduction lens magnify the image in the position sensing direction on the detector and the field lens provides for a relatively large field of view. The detector is a photodetector such as a lateral effect photodiode or a rectangular lateral effect detector. A pre-amplifier provides a pair of electrical signals which are utilized for signal processing circuitry to compute the centroid for the light spot.

A line of image data, covering multiple pins or balls, is provided at high rates (approximately 2000 lines per second). Each line provides 512 points of eight bit height data as well as eight bits of intensity (gray scale) data used to determine the position of the pin or ball grid in the direction of the electronic scan.

The three-dimensional scanner 16 typically has a resolution (pixel size) in the X axis of 0.001 inch and in the Z axis of 0.00025 inch for ball grid arrays and 0.001 inch for pin grid arrays. This results in a 0.064 inch range for ball grid arrays and 0.256 inch range for pin grid arrays. However, the X and Z pixel sizes can be modified by making minor adjustments to the electronics of the system. The three-dimensional scanner 16 has a scanning speed of at least 512 pixel scan lines per 0.0005 seconds (i.e., at least 1,200,000 Pixels/second). The position of the laser beam is controlled by laser electronics 30 and the driver for the solid state (acousto-optic) device.

Since the three-dimensional scanner 16 scans only in one dimension and the grid arrays 12 are larger than the scan width of the three-dimensional scanner system 16, the three-dimensional scanner 16 must be moved to provide full coverage of the grid array 12. Thus, the three-dimensional scanner 16 is mounted on a metrology-grade positioning system 20. The metrology-grade positioning system 20 includes the three-dimensional scanner 16, a scanner positioning stage 22, a granite base 24, and control electronics 26 for controlling the position of the stage 22. Since the motion of the three-dimensional scanner 16 directly affects the accuracy of the data, the positioning stage 22 must be controlled accurately and have a high resolution.

Figure 2:
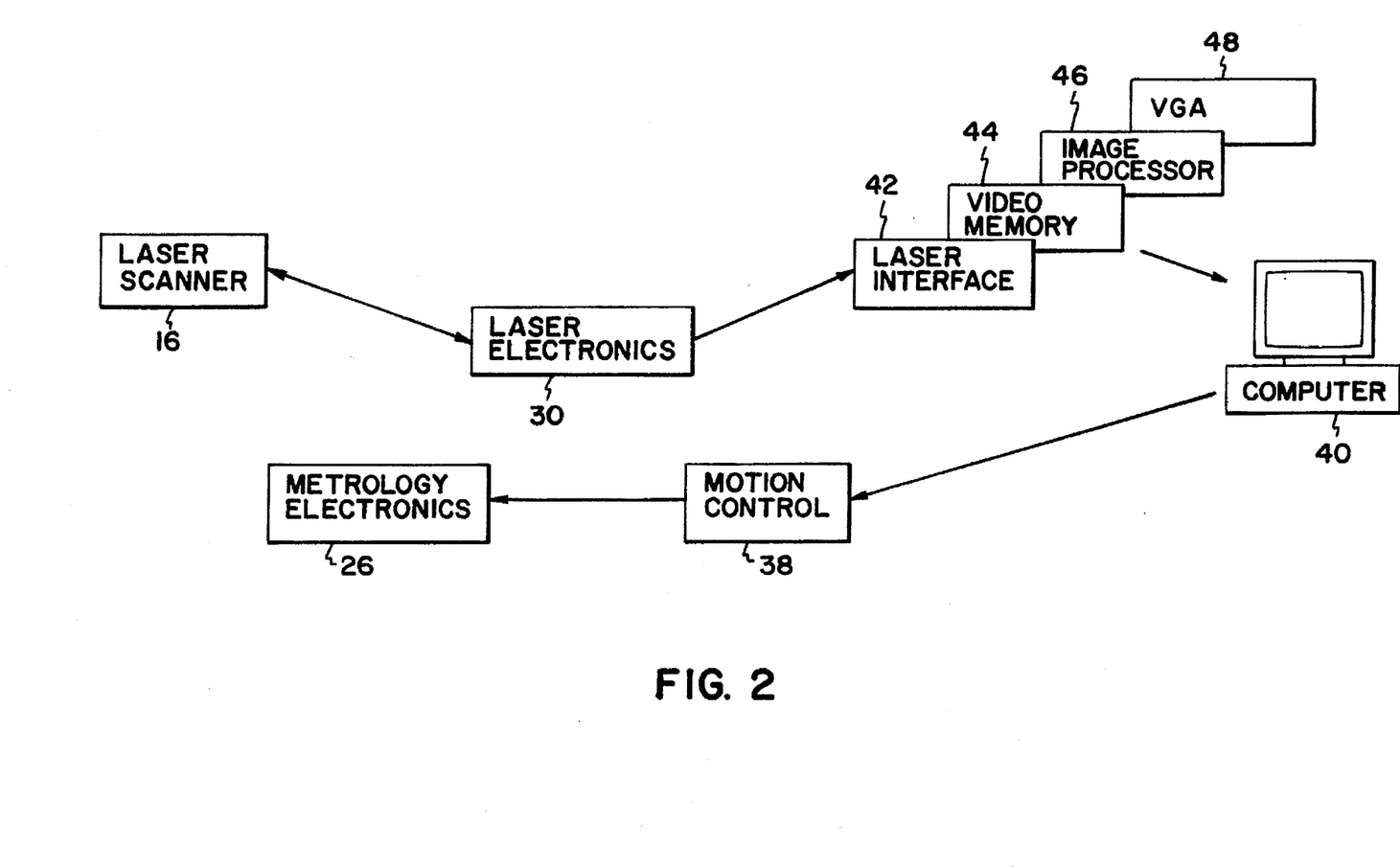
FIG. 2 is a block diagram of the grid array inspection system.

FIG. 2 illustrates a block diagram of the inspection system. The control electronics 26 of the metrology unit are driven by a precision motion control unit 38 which receives and interprets commands from a computer 40. The particular scanner positioning stage 22 provides a range of motion which can be varied according to need. In the preferred embodiment, the stage has a range of motion of 8 inches in the X direction and 4 inches in the Y direction with 0.1 micron resolution.

A separate scanner interface 42 provides high speed image acquisition and timing. The video memory board 44 is used to store image data from the scanner 16 and to perform bit manipulation of the image. Data from the video memory 44 is sent to the optional image processor 46 and overlaid with the VGA graphics 48 for displaying the images on computer 40. The computer 40 is used to manipulate the collected data. The grid array inspection system 10 thereby can provide two dimensional (intensity) data and a three dimensional (height) data. All control electronics including the computers are housed in the base 20.

Figure 3:
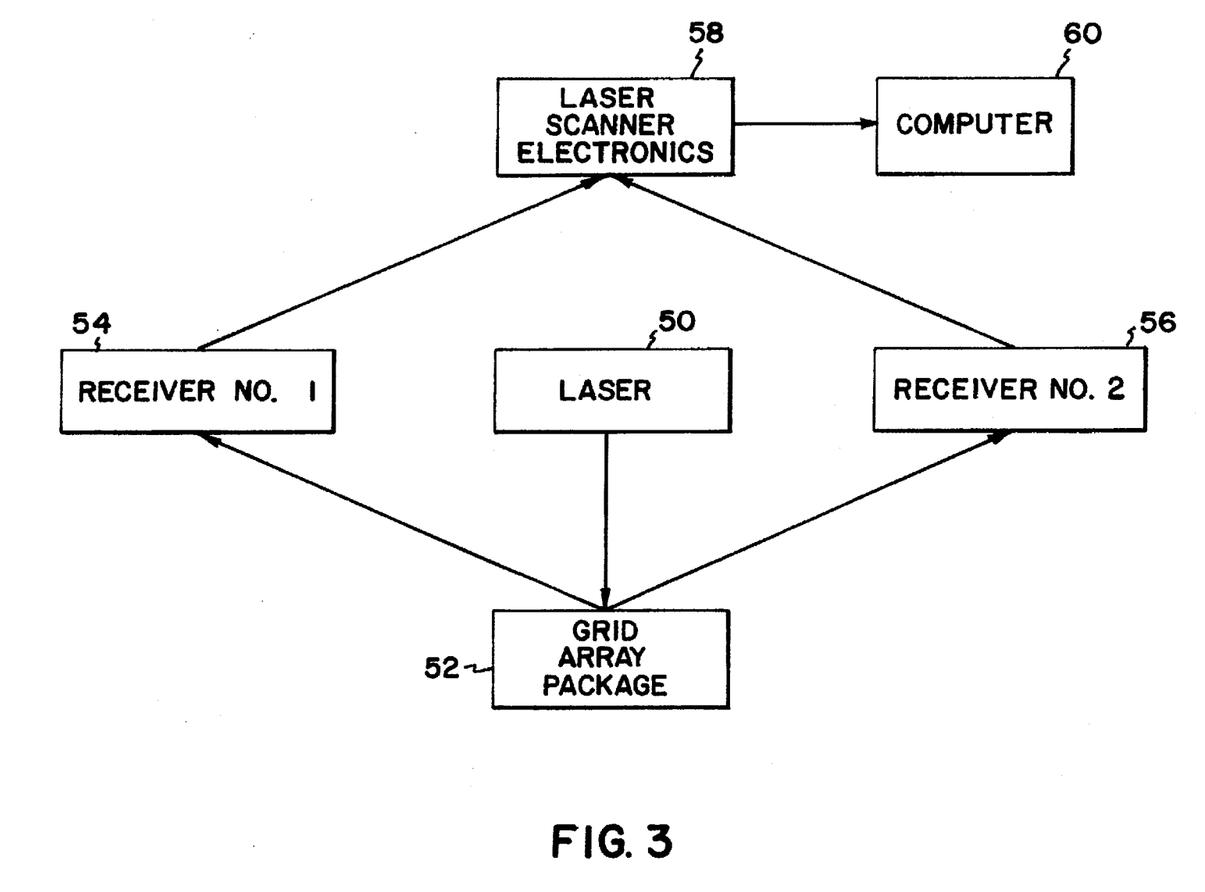
FIG. 3 is a block diagram of the dual detector utilized in one embodiment of the invention.

FIG. 3 illustrates a dual detector configuration which may be utilized to further eliminate occlusion effects and reduce specular reflections and errors caused by secondary reflections. A laser 50 scans across a grid array package 52. Receiver #1 54 and Receiver #2 56 collect the scanned image and route the information to the laser scanner electronics 58. Thereafter, the image is routed to the computer 60 for displaying.

Pin Grid Array Inspections

Figure 4:
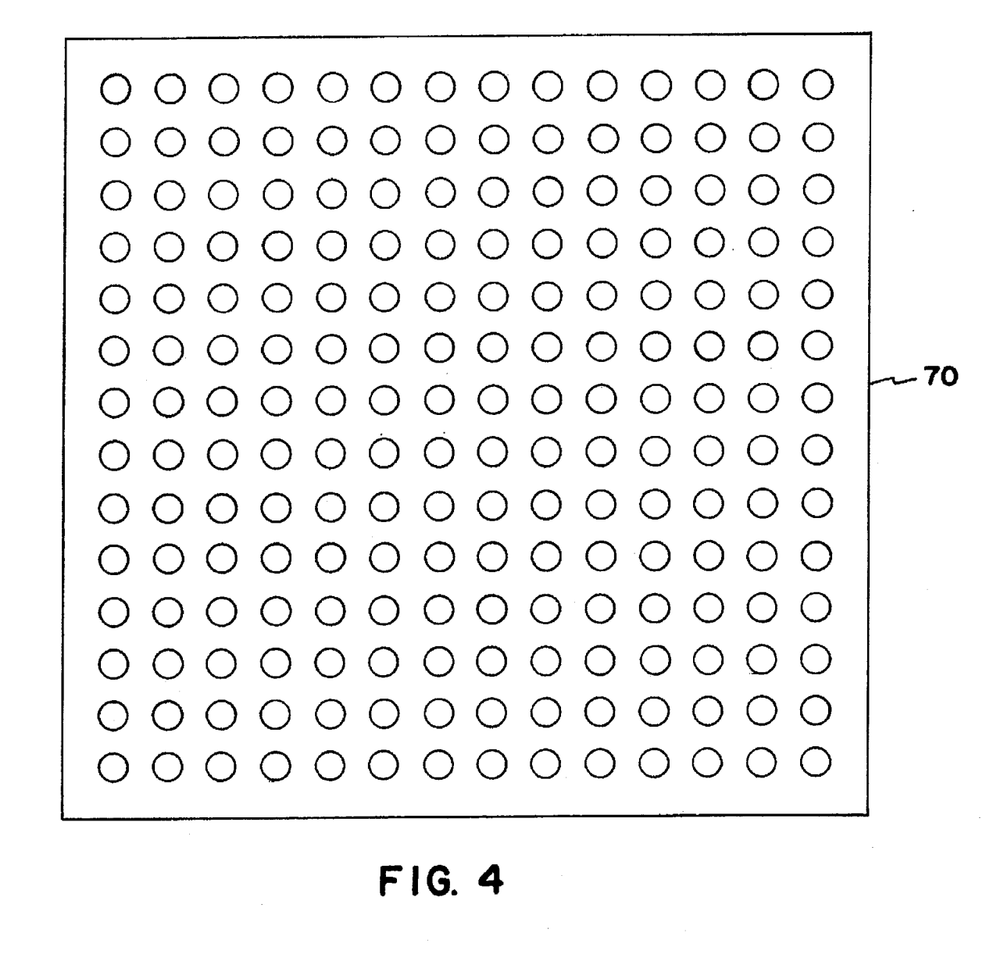
FIG. 4. is plan view of a pin grid array package.

In one embodiment of the present invention, the grid inspection assembly gathers data pertaining to pin grid assemblies 70 as illustrated in FIG. 4. The inspection system 10 performs high speed, high accuracy data collection pixel-by-pixel for the image illuminated by the three-dimensional scanner 16.

Figure 5A:
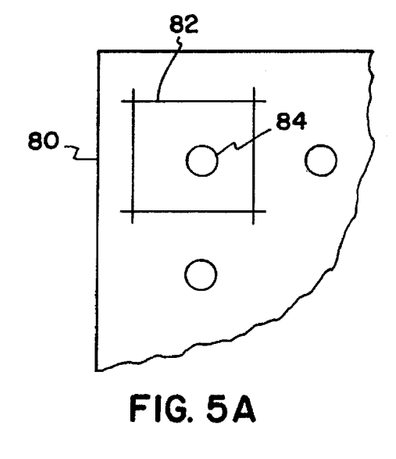
FIGS. 5A–5C illustrate the method used by the grid array inspection system to locate a pin.
Figure 5B:
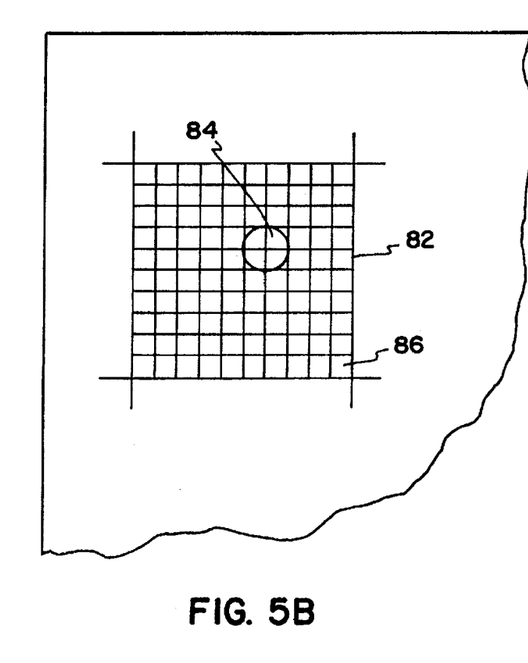
Figure 5C:
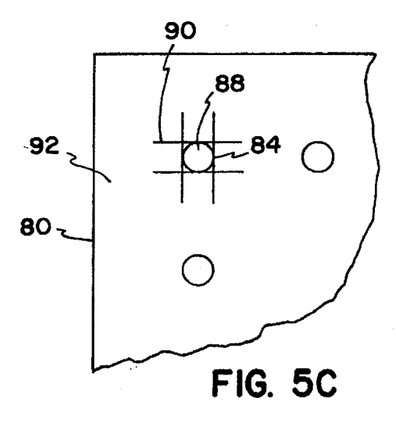

Referring to FIGS. 5A–5C, the determination of pin positions will be described. The operator first identifies the type of pin grid array being inspected and enters the identification code into the computer. As illustrated in FIG. 5A, the computer matches the identification code to a coarse alignment grid 82 from a data file.

Referring to FIG. 5B, the coarse position grid 82 consists of a block of predetermined dimension containing pixel data representing the height measurement for each pixel 86. Each pixel 86 represents roughly a 0.001 inch by 0.002 inch area. Pin 84 height levels are based on 0.001 inch per level of gray scale. The gray scale ranges from 0 to 255 therefore a pin height of 0 to 0.255 inches is capable of being measured.

The individual values representing the height data for that pixel 86 facilitates the determination of the height and physical location of each pin 84. FIG. 5C illustrates the location of the tip 88 of a pin 84. Once the coarse position of a pin 84 is located, the algorithm performs a fine search 90 of the image for pixels 86 which represent the tip 88 of the pin 84. The height value for the tip 88 of the pin 84 will be significantly greater than the surrounding height values representing the bottom surface 92 of the grid array package 80. Once the height and position data is determined, coplanarity and regression plots can be developed and analyzed. Limits can be set within the algorithm such that the grid array package can be rejected based upon the detection of deviations from the boundary limits with respect to height, position, coplanarity, and regression.

Figure 6A:
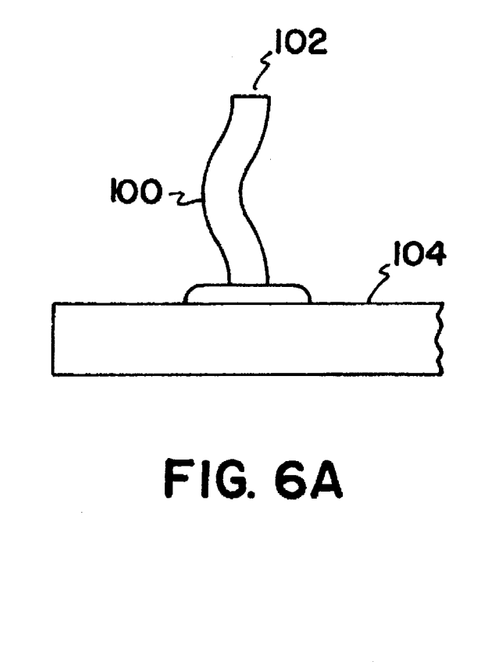
FIGS. 6A and 6B illustrate a side view and a plan view, respectively, of a pin experiencing a compound bend.
Figure 6B:
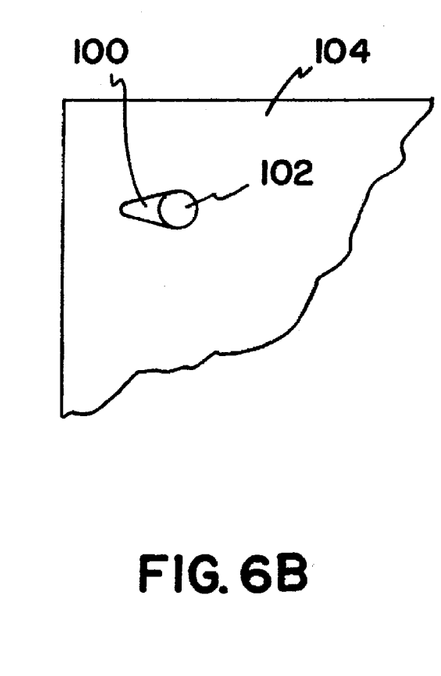

FIG. 6A illustrates a side view of a typical compound bend 100. Two-dimensional and three-dimensional image processing of the present invention enables the detection of compound bends 100 in pins 102 on pin grid array packages 104. FIG. 6B illustrates a top view of a compound bend 100. Compound bends are generally characterized by height data in the range between what the base of the pin grid array shows and that of the tip. The sensor does not always accurately detect the compound bend from the height data due to the nearly vertical slope of the lead which scatters the laser energy. But due to this phenomenon, the two-dimensional (intensity) image of a compound bend can be characterized by a dark region where the compound bend is. The compound bend detection techniques therefore exploit both the two-dimensional (intensity) imagery as well as the three-dimensional (height) imagery.

Figure 7:
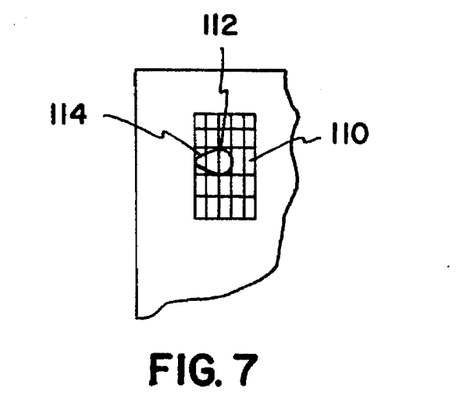
FIG. 7 illustrates a first and second method of locating the position of a pin experiencing a compound bend.

Five methods are currently used to identify compound bends. FIG. 7 illustrates the first method which uses an algorithm to analyze the height levels between pixel 110 values around the identified tip 112 of the pin in the three-dimensional image. Using histogram techniques, the algorithm identifies the compound bend 114 as existing when there is a relatively large number of high pixels in the area of interest around the pin.

The second method is similar to the first but analyzes the intensity image. Using histogram techniques, the algorithm identifies a compound bend when there is a relatively large number of dark pixels in the area of interest.

Figure 8:
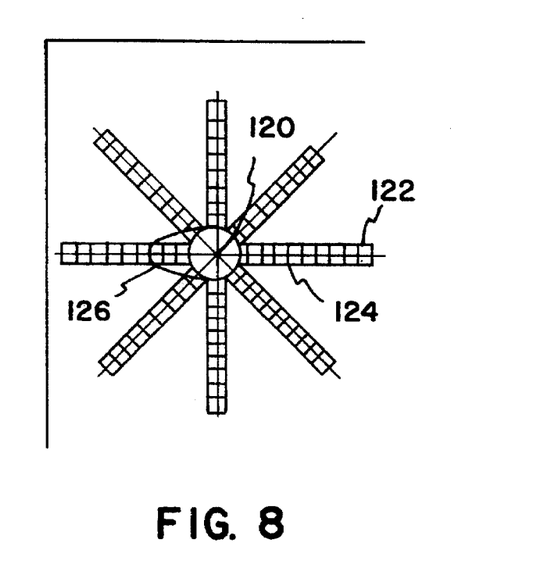
FIG. 8 illustrates a third and fourth method for locating the position of a pin experiencing a compound bend.

FIG. 8 illustrates the third method which involves performing a radial profile measurement around the tip 120 of the pin in the three-dimensional image. The height pixel value 122 along a line 124 of pixels extending outward away from the tip 120 of the pin is added. The sum of the height pixel values (Z profile) along each line will be approximately the same except where the compound bend exists 126. In the radial profile line encompassing the compound bend, the level will deviate from the other radial profile values due to the high pixel values representing the portion of the pin protruding from the axis.

Figure 9:
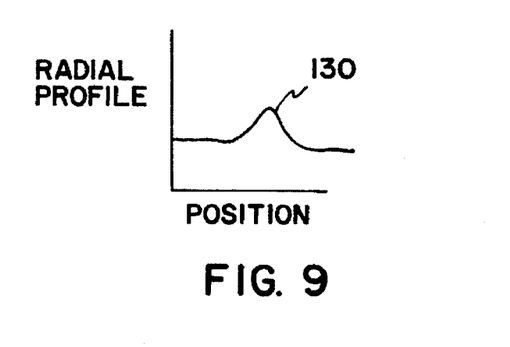
FIG. 9 is a plot of the radial profile resulting from the third method for locating the position of a pin experiencing a compound bend.

FIG. 9 illustrates a plot of the radial profile. The plots illustrates a smooth curve having an upward protrusion 130 at the location of the compound bend.

The fourth method is similar to the third method, but uses intensity data instead. The radial profiles are analyzed to find the lowest values. A relatively low value is indicative of a probable compound bend.

Figure 10:
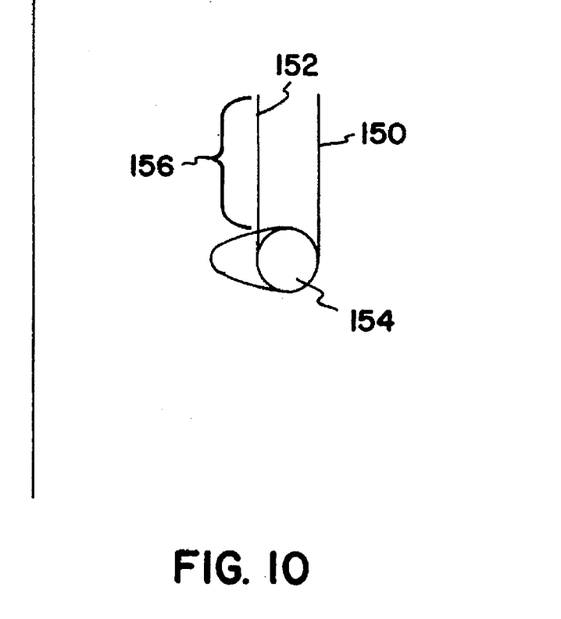
FIG. 10 illustrates the tangential profile method for locating the position of a compound bend.
Figure 11:
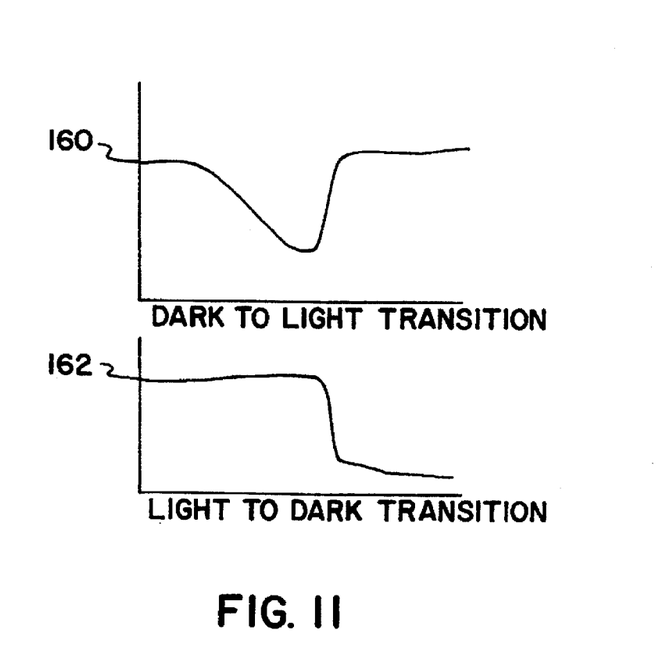
FIG. 11 is a plot of the dark to light and light to dark transitions obtain from the radial profile method.

The final method involves performing tangent profile measurements around the tip. FIG. 10 illustrates this method. Two lines of pixels 150,152 substantially tangent to the tip of the pin 154 and parallel to one another are selected. The height values for each pixel represented by the portion 156 of the tangent extending beyond the tip and to one side of the pin 154 are added. The orientation of the tangents are rotated around the pin 154 and additional measurements are taken. The tangent profiles are computed and result in a dark to light transition plot and a light to dark transition plot. FIG. 11 illustrates the plot of the light to dark 160 and dark to light 162 transitions. The location of a compound bend is found at the edge of the transitions in the plots. By using the first derivative of these light to dark and dark to light edges, positions are determined and compared, thereby increasing the reliability of the compound bend identification. The location of the compound bend 130 occurs where a transition from dark to light aligns with a transition from light to dark. The tangent profile method results in a substantially better indication of the location of subtle compound bends than other methods.

The location parameters from the five methods are combined using fuzzy logic to weigh each method. The most distinctive identification of a compound bend relies on the tangent profile and Z profile method. Thus, in the preferred embodiment, the first, second and fourth methods are given a weight of zero or near zero. However, it should be understood, that the weight values given to the other methods could be modified.

Ball Grid Array Inspections

In another embodiment of the invention a ball grid assembly is inspected. As with the previous embodiment, the operator first identifies the type of ball grid array being inspected and enters the identification code into the computer. The computer again matches the identification code to a coarse alignment grid from a data file.

After the coarse location of each ball is identified, the position of each solder ball is located by matching X and Y projections (profiles).

Figure 12:
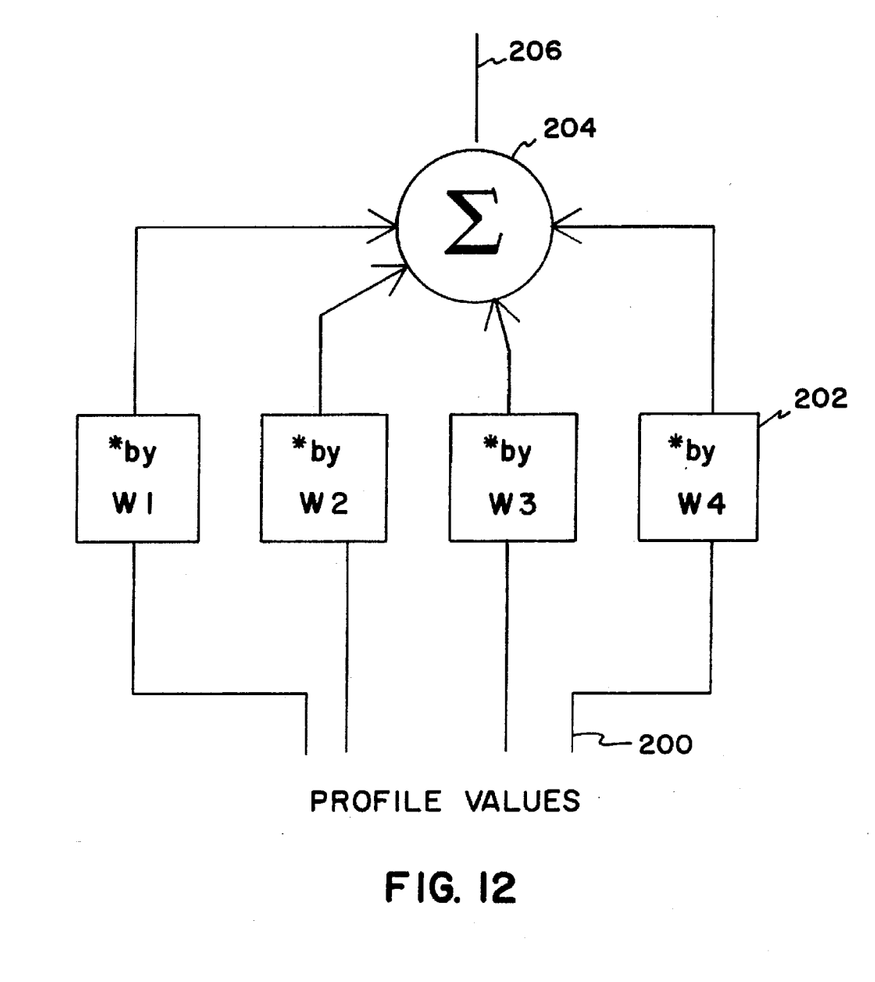
FIG. 12 illustrates the method for finding the location of a ball grid.

FIG. 12 illustrates the method for finding the location of a ball grid. The matching is performed by taking each profile entry 200, multiplying it by a weighting factor 202, and adding 204 the resulting products. This process is repeated for each potential location and the location corresponding to the greatest sum represents the position of the solder ball. A three sample interpolation is used to get sub-pixel location. This process is the same for both X and Y profiles.

The algorithm used for finding the position of a ball is similar to an artificial neural net algorithm, but with only one neuron. In neural net terms it would be called a single element, single layer perceptron. The weighting factors 202 are optimized to give a high output 206 when the position of the ball is located. The optimization of the weighting factors 202 is performed using the Widrow-Hoff equation. The Windrow-Hoff equation is equivalent to the back propagation algorithm when there is only one neuron.

Figure 13:
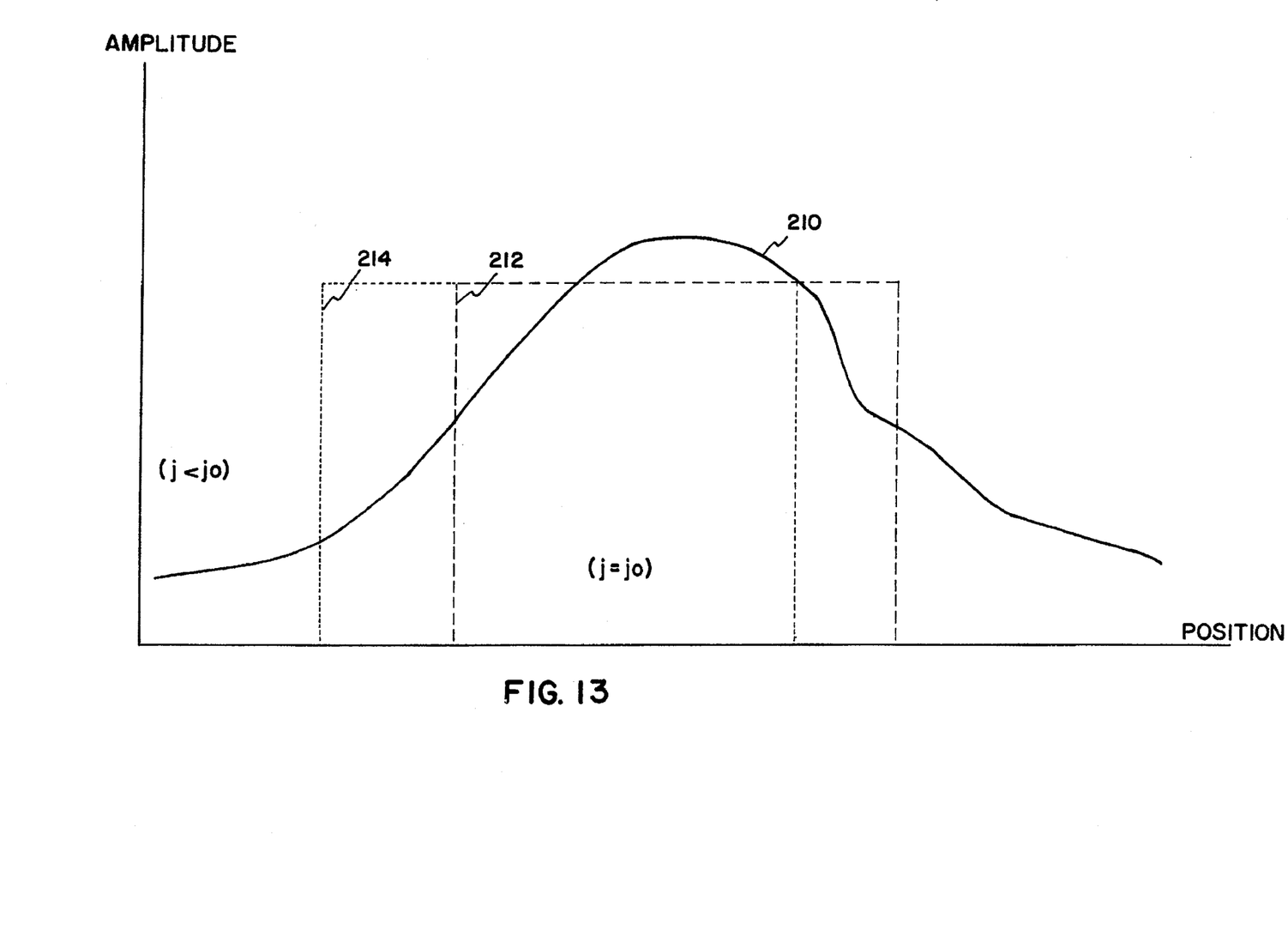
FIG. 13 shows a profile for a ball and an aligned and unaligned window.

FIG. 13 shows a typical profile for a ball 210 as well as an aligned 212 and unaligned window 214. The length of the window is dependent upon the number of inputs to the perceptron. The perceptron provides a positive output when the window is aligned 212, and a negative output when the window is not aligned 214.

The output of the perceptron at window position j is given by $$O_j = \sum_{i=1}^{N} W_i P(i+j)$$

where N is the number of inputs to the perception, P(i) is the ith element in the profile, and $W_i$ is the ith coefficient for the perceptron.

The weighting factors are optimized to cause the window to be aligned with the position of the solder ball. When the window is aligned with the position of the solder ball, $j=j_o$, and $O_j$ is equal to 1. When the window is not aligned with the position of the solder ball, $O_j$ is equal to $-1$. Thus, the output of the perceptron is positive only when the window is aligned. The adaptation process uses these values as desired outputs, and adjusts the coefficient according to the Widrow-Hoff equation. The Widrow-Hoff equation is expressed as follows:

$$W_{i,n+1} = W_{i,n} + \mu(D_j - O_j) P(i+j)$$

where $D_j$ is the desired output at offset j, and $\mu$ is a constant that sets the adaptation speed. The n and n+1 double subscript on W indicates the value before and after an iteration. The Widrow-Hoff rule is applied repeatedly to optimize the weighting coefficients.

Once the exact position of a solder ball is located, the height of each solder ball can be determine. Thereafter, coplanarity and regression data can be gathered and the ball grid assembly analyzed for deviations from desired specifications. In addition to the height and position measurements, the grid array inspection system can also measure element spacing, lead height, coplanarity, standoff, grid pitch, ball diameter, ball position, and package warp from the height and position data.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is:

1. An apparatus for inspecting a grid array, comprising:
   (a) a three-dimensional laser scanner for projecting and scanning a beam of laser light across the grid array;
   (b) collection means for collecting light scattered from the grid array by the beam of laser light to generate a first set of three-dimensional and intensity information;
   (c) a computer for controlling the laser scanner and collection means and for receiving the first set of three-dimensional and intensity information, the computer further comprising:
      (i) means for storing the first set of three-dimensional and intensity information into the computer; and
      (ii) data processing means for extracting height and dimensional data for the grid array from the first set of three-dimensional and intensity information;
   (d) coarse position determining means, coupled to the data processing means, for analyzing the extracted dimensional data to generate a coarse position location for a grid array element; and
   (e) fine position determining means, coupled to the data processing means, for analyzing the extracted height data to generate a fine position location for the grid array element.

2. The apparatus of claim 1, wherein the collection means further comprises a dual detector means for receiving the scattered light from the beam of laser light to generate a first set of three-dimensional and intensity information.

3. The apparatus of claim 1, wherein the grid array is a pin grid array having parallel connector pins extending away from the surface of the grid array, the pins comprising a base attached to the array surface, a shaft extending from the base and a tip at the end of the shaft, wherein the fine position determining means further comprises means for determining the position of the tip of each pin within the coordinates of the coarse position.

4. The apparatus of claim 3, wherein the means for determining the position of the tip of each pin further comprises means for determining the height of the tip of each pin on the pin grid array.

5. The apparatus of claim 4, wherein the means for determining the height of each pin further comprises means for determining the mean value of the pin tip heights and means for determining the amount of deviation of each pin from the mean height value.

6. The apparatus of claim 3, wherein the means for extracting height and positional data further comprises means for determining the location of a pin experiencing a compound bend.

7. The apparatus of claim 6, wherein the means for determining the location of a pin experiencing a compound bend further comprises:

first means for determining a first location of a compound bend by comparing the three-dimensional information around the tip of the pin, the first location being where high three-dimensional values are detected;

second means for determining a second location of the compound bend by comparing the intensity information around the tip of the pin, the second location being where low intensity values are detected;

third means for determining a third location of the compound bend from a radial profile of a line extending radially from the tip of the pin, the radial profile comprising the sum of the three-dimensional information along the line, the third location of the compound bend being where the radial profile is greatest;

fourth means for determining a fourth location of the compound bend from a radial profile of a line extending radially from the tip of the pin, the radial profile comprising the sum of the intensity information along the line, the fourth location of the compound bend being where the radial profile is the lowest; and fifth means for determining a fifth location of the compound bend by determining the tangential profile of two parallel lines tangent to the tip of a pin, the tangential profile being the sum of the three-dimensional information along the tangent, the fifth location of the compound bend being where the gradient of the tangential profile of the two parallel tangential lines is the greatest and where the gradient of the tangential profiles of the two parallel tangential lines match each other;

means for assigning a weight value to each of the locations obtain from the first through fifth location determining means; and means for summing the product of the weight values and the location for each location determining means.

8. The apparatus of claim 7, wherein the weight value assigned to each location obtained from the first, second and fourth location determining means is zero.

9. The apparatus of claim 1, wherein the grid array is a ball grid array, wherein the fine position determining means further comprises means for determining the position of the tip of each ball within the coordinates of the coarse position.

10. The apparatus of claim 9, wherein the means for determining the position of the tip of each ball further comprises:

neural net means for summing the product of weighting factors and height values received by the neural net means according to:

$$O_j = \sum_{i=1}^{N} W_i P(i+j)$$

where N is the number of height value inputs to the neural net, P(i) is the ith height value and j is the position of the window, the width of the window being the number of height value inputs to the neural net; and means for updating the weighting factors according to:

$$W_{i_{n+1}} = W_{i_n} + \mu (D_j - O_j) P(i+j)$$

where $D_j$ is the desired output at offset j, and $\mu$ is the adaptation speed, the updating process being repeated until the window is aligned, the window being aligned when the output $O_j$ of the neural net means is positive.

11. The apparatus of claim 10, wherein the means for determining the position of the tip of each ball further comprises means for determining the distance the apogee of each ball extends from the surface of the grid array.

12. The apparatus of claim 11, wherein the means for determining the distance each ball extends from the surface of the grid array further comprises means for determining the mean value of the ball apogees and means for determining the amount of deviation of each ball apogee from the mean apogee value.

* * * * *